United States Patent [19]

Tjoeng et al.

[11] Patent Number: 4,716,147

[45] Date of Patent: Dec. 29, 1987

[54] SYNTHETIC AIRIAL PEPTIDES

[75] Inventors: Foe S. Tjoeng, Manchester; Kam F. Fok, St. Louis; Steven P. Adams, St. Charles, all of Mo.

[73] Assignee: Monsanto Company, St. Louis, Mo.

[21] Appl. No.: 844,906

[22] Filed: Mar. 27, 1986

[51] Int. Cl.$^4$ .................. A61K 37/02; C07K 7/10; C07K 7/08
[52] U.S. Cl. ........................ 514/11; 514/13; 514/12; 530/324; 530/325; 530/326
[58] Field of Search ............... 530/324, 325, 326; 514/11, 12, 13

[56] References Cited

U.S. PATENT DOCUMENTS 4,496,544  1/1985  Needleman ................. 514/13
4,508,712  4/1985  Needleman ................. 514/11

OTHER PUBLICATIONS

Currie et al., Science 223, 67–69, (1984).
Geller et al., Biochem. Biophys. Res. Commun., 120(2), 333–8, (1984).
Wakitani et al., J. Lab. Clin. Med., 105(3), 349–352, (1985).
Flynn et al., Biochem. Biophys. Res. Commun., 117(3), 859–65, (1983).
Seidah et al., Proc. Natl. Acad. Sci. USA 81, 2640–44, (1984).
Schwartz et al., Science, 229, 397–400, (1985).
Thibault et al., Biochem. Biophys. Res. Commun., 125(3), 938–46, (1984).
Garcia et al., Ibid., 126(1), 178–184, (1985).
Katsube et al., Ibid., 128(1), 325–30, (1985).
Johnson, Life Sci., 38(3), 225–31, (1985).
Kangawa et al., Biochem. Biophys. Res. Commun., 118(1), 131–139, (1984).

*Primary Examiner*—Delbert R. Philips
*Attorney, Agent, or Firm*—Scott J. Meyer; James W. Williams, Jr.

[57] ABSTRACT

Novel synthetic atrial peptides are provided with enhanced natriuretic properties by substituting one or two arginine residues for the N-terminal ser-ser in atriopeptins I, II and III and their physiologically acceptable salts, esters and amides.

16 Claims, No Drawings

SYNTHETIC AIRIAL PEPTIDES

BACKGROUND OF THE INVENTION

This invention relates to novel synthetic atrial peptides having useful natriuretic activity.

In recent years, considerable research investigation has been made on the atrial peptides. These are polypeptide hormones which were originally extracted from the heart atrial muscle. They have been denoted by various terminology such as cardionatrin, atrial natriuretic factor (ANF), atriopeptin (AP), atriopeptigen, auriculin and cardiodilatin. Biological activity has been shown with these peptides having amino acid chain lengths from as short as about 18 amino acids to as long as over 150 amino acids. The biological activity includes diuretic, natriuretic, smooth muscle relaxing, blood pressure lowering and other such properties having an important role in the regulation of volume balance, sodium homeotasis and vascular tone.

A great number of detailed articles have been published on the structure and biological properties of various of the atrial peptides. For brief background information on the atrial peptides in general, reference can be had to the following recent publications and the references cited therein:

Sagnella and MacGregor, Nature 309, 666–667 (1984);
Palluk et al., Life Sci. 36 (15), 1415–1425 (1985);
Needleman et al., Hypertension 7(4), 469–482 (1985); and
de Bold, Science 230, 767–770 (1985).

An important group of atrial peptides of significant interest, known as Atriopeptins I, II and III (AP-I, AP-II and AP-III), are described, for example, by Currie et al. Science 223, 67–69 (1984); Geller et al., Biochem. Biophys. Res. Commun. 120(2), 333–338 (1984); and Needleman, U.S. Pat. No. 4,496,544. These peptides in the oxidized (cyclized) form have the following amino acid sequences:

ATRIOPEPTIN I
```
1
Ser—ser—cys—phe—gly—gly—arg—ile—asp—arg—ile—gly—ala—gln—ser—gly—
            |                                                        21
leu—gly—cys—asn—ser
```

ATRIOPEPTIN II
```
1
Ser—ser—cys—phe—gly—gly—arg—ile—asp—arg—ile—gly—ala—gln—ser—gly—
            |                                                        23
leu—gly—cys—asn—ser—phe—arg
```

ATRIOPEPTIN III
```
1
Ser—ser—cys—phe—gly—gly—arg—ile—asp—arg—ile—gly—ala—gln—ser—gly—
            |                                                        24
leu—gly—cys—asn—ser—phe—arg—tyr
```

It is known that loss of the carboxy-terminal phe-arg from AP-II markedly suppresses the vasodilator activity whereas extension of the C-terminal phe-arg-tyr of AP-III does not enhance vascular reactivity. See Wakitani et al., J. Lab. Clin. Med. 105(3), 349–352 (1985).

Extensions of these peptides at the amino-terminal also are known, for example,
Ser-leu-arg-arg-AP-III and
Arg-arg-AP-III.
See Flynn et al., Biochem. Biophys. Res. Commun. 117(3), 859–865 (1983); and Seidah et al., Proc. Natl. Acad. Sci. USA 81, 2640–2644 (1984). Ser-leu-arg-arg-AP-III has been described as the major circulating form of atrial peptide. Schwartz et al., Science 229, 397–400 (1985).

Differential structure-activity relationships of these atrial peptides as natriuretics and renal vasodilators has been discussed, for example, by Thibault et al., Biochem. Biophys. Res. Commun. 125(3), 938–946 (1984); Garcia et al., Ibid. 126(1), 178–184 (1985); Katsube et al., Ibid. 128(1), 325–330 (1985); and Johnson, Life Sci. 38(3), 225–231 (1985).

As distinguished from the rat-derived atrial peptides, the human-derived analogs contain methionine instead of isoleucine in position number 8 in the above sequences for AP-I, II and III. See, for example, Kangawa et al., Biochem. Biophys. Res. Commun. 118(1), 131–139 (1984).

BRIEF DESCRIPTION OF THE INVENTION

In accordance with the present invention it has now been found that substitution of the N-terminal $Ser^1$-$ser^2$ in AP-I, II, III and related atrial peptides by one or two arginine residues results in enhanced biological activity. This improved activity was surprising and unexpected since analogous substitution with other positively charged amino acids, namely lysine and histidine, did not improve activity but, instead, reduced the activity of the atrial peptides. Moreover, substitution with arginine in the position immediately following rather than preceding the first cysteine residue likewise reduced rather than enhanced the activity.

Thus, the novel synthetic peptides of this invention have the following amino acid sequence:

$$R_1\text{-cys-phe-gly-gly-arg-X-asp-arg-ile-gly-ala-gln-ser-gly-leu-gly-cys-asn-}R_2$$

wherein $R_1$ = arg, arg-arg, leu-arg-arg, ser-leu-arg-arg, D-arg, D-arg-D-arg, $R_2$ = OH, ser, ser-phe, ser-phe-arg, ser-phe-arg-tyr, and X = ile or met, or the physiologically acceptable salts, esters or amides thereof.

The preferred synthetic atrial peptides as above-defined contain an internal disulfide ring produced by a bond between sulfur atoms in the two cysteine residues. Substitution with the L-arginine stereoisomer is generally preferred to substitution with the D-arginine stereoisomer in the $R_1$ position. The amide form of the peptide is preferred to the free acid form. A most preferred amide is a mono- or di-lower alkyl substituted amide in which lower alkyl is $C_{1-3}$ alkyl, for example, ethylamide.

The general reaction sequence for conventional Merrifield peptide synthesis can be illustrated as follows.

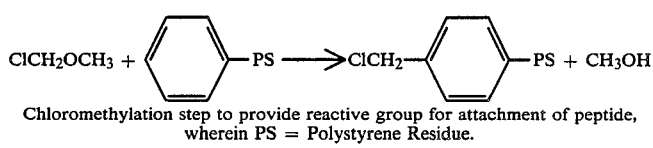

I. Chloromethylation step to provide reactive group for attachment of peptide, wherein PS = Polystyrene Residue.

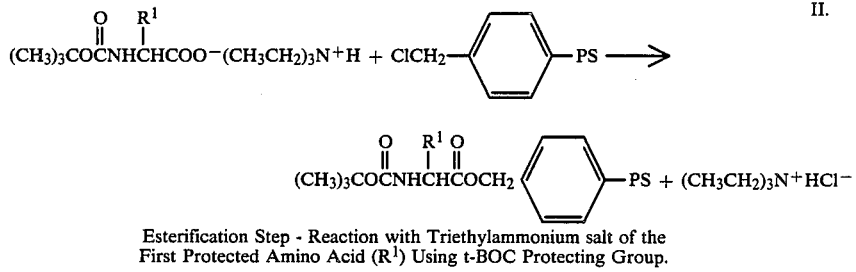

II. Esterification Step - Reaction with Triethylammonium salt of the First Protected Amino Acid ($R^1$) Using t-BOC Protecting Group.

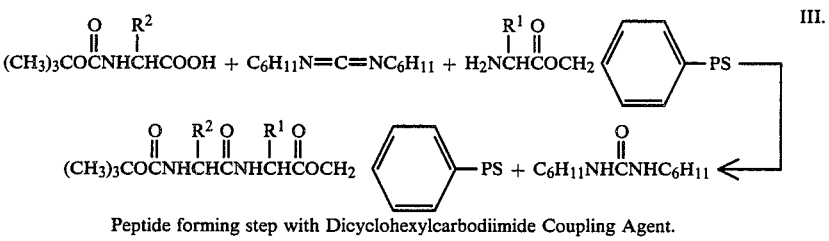

III. Peptide forming step with Dicyclohexylcarbodiimide Coupling Agent.

DETAILED DESCRIPTION OF THE INVENTION

The synthetic atrial peptides of this invention can be made by appropriate adaptation of conventional methods for peptide synthesis. Thus, the peptide chain can be prepared by a series of coupling reactions in which the constituent amino acids are added to the growing peptide chain in the desired sequence. The use of various N-protecting groups, e.g., the carbobenzyloxy group or the t-butyloxy-carbonyl group (BOC), various coupling reagents, e.g., dicyclohexylcarbodiimide or carbonyldiimidazole, various active esters, e.g., esters of N-hydroxy-pthalimide or N-hydroxysuccinimide, and various cleavage reagents, e.g., trifluoracetic acid, HCL in dioxane, boron tris(trifluoracetate) and cyanogen bromide, and reaction in solution with isolation and purification of intermediates is well-known classical peptide methodology.

Preferably, the peptides of this invention are prepared by the well-known Merrifield solid support method. See Merrifield, J. Amer. Chem. Soc. 85, 2149-54 (1963) and Science 150, 178-85 (1965). This procedure, though using many of the same chemical reactions and blocking groups of classical peptide synthesis, provides a growing peptide chain anchored by its carboxyl terminus to a solid support, usually cross-linked polystyrene or styrene-divinylbenzene copolymer. This method conveniently simplifies the number of procedural manipulations since removal of the excess reagents at each step is effected simply by washing of the polymer.

This step III follows cleavage of t-BOC such as by treatment, for example, with 50% trifluoroacetic acid in methylene chloride and liberation of N-terminal amine by excess of triethylamine, thereby enabling it to react with the activated carboxyl of the next protected amino acid ($R^2$). A final step involves cleavage of the completed peptide from the PS resin such as by treatment, for example, with anhydrous HF in anisole or anhydrous HBr in acetic and or trifluoracetic acid.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in Advances in Enzymology 32, pp. 221-296, F. F. Nold, Ed., Interscience Publishers, New York, 1969; and Erickson and Merrifield, The Proteins, Vol. 2, p. 255 et seq. (ed. Neurath and Hill), Academic Press, New York, 1976.

The biological activity of the synthetic atrial peptides of this invention was determined by an in vitro assay which measures relaxation of vascular smooth muscle (rabbit aorta), and by in vivo assay in dogs for monitoring renal blood flow, urine flow and increase of sodium excretion in the urine.

The rabbit aorta relaxation assay (RA) was carried out essentially by the procedure of Currie et al., Science 221, 71-73 (1983) using rat atriopeptin III = 1.0 as the control standard. According to this bioassay, spiral strips of rabbit thoracic aorta are continuously perfused with oxygenated Krebs-Henseleit solution at 37° C. and maintained in tone by continuous infusion of norepinephrine at $4.5 \times 10^{-8}$M concentration. The effects of test peptides are then determined by application of the test peptide in buffered saline solution with micropipets to the stream of medium flowing over the aorta tissues. The relaxation in mm of the treated strip is measured after a given period of time, for example, 30 minutes, and compared against the control standard.

The renal function tests in dogs were carried out essentially by the procedure described by Katsube et al., *Biochem. Biophys. Res. Commun.* 128(1), 325–330 (1985) using rat atriopeptin III=1.0 as the control standard. In the canine renal function tests, pentobarbital anesthetized beagle dogs were subjected to intrarenal artery injection of the test peptides at four levels in physiological saline solution to obtain a dose response curve and compared against the control standard at similar doses. The control standard produced concentration dependent increases in renal flow (RF) using an electromagnetic flow probe and sodium excretion, ($U_{Na}V$) as determined by flame photometry.

The control standard in these bioassays was atriopeptin III. The biological activity of the test peptides in each instance was determined relative to the corresponding activity of the control standard which was assigned a value of 1.0.

The following examples will further illustrate the invention in greater detail although it will be appreciated that the invention is not limited to these specific examples.

In these examples, the peptide molecules were synthesized on 1% cross-linked polystyrene resin supports by the classical solid phase method of Merrifield as cited above. 4-methylbenzyl hydrylamine resin was similarly used for synthesizing the peptide amides. In order to prepare the alkylamide form of the peptide, the Merrifield resin was pretreated with alkylamine, for example, ethylamine, prior to the peptide synthesis.

A standard synthetic cycle is depicted in Table 1, below. In general, the coupling rates of Boc-amino acid (having the N-protecting group t-butyloxy-carbonyl) with the growing peptide chain varied depending on the nature of the substrate, so the peptide resin was monitored by the ninhydrin color reaction test, Kaiser et al., *Anal. Biochem.* 34, 595–598 (1970), to determine when the reaction was complete. In the event that the reaction was incomplete, the resin was recoupled with a new charge of Boc-amino acid and coupling agent dicyclohexylcarbodiimide (DCC). N-protected amino acids used in the synthesis were Boc-Ser(Bzl), Boc-Cys(4-MeBzl), Boc-Phe, Boc-Gly, Boc-Arg(Tos), Boc-Ile, Boc-Met, Boc-Asp(OBzl) Boc-Ala, Boc-Gln, Boc-Leu, Boc-Asn, Boc-Tyr-(2,6-diClBzl); the resins were chlormethylated polystyrene for peptide acids and 4-methylbenzhydrylamine for peptide amides. Peptides were deprotected and removed from the resin by treatment with HF, and were purified by high pressure chromatography using a μ Bondapak reverse phase column eluting with a gradient of 15% to 30% acetonitrile in water (both solvents buffered with 0.05% trifluoroacetic acid). The purity of the peptide was monitored by analytical reverse phase HPLC on a Vydac column (The Separations Group, Hesperia, Calif.). The peptides were oxidatively cyclized (disulfide formation between the cysteine residues) by stirring the purified peptide open to the air in pH 7.8 ammonium bicarbonate buffer. The progress of the cyclization was monitored by analytical HPLC and when completed, the peptide was purified on the high pressure column described above. The final product was lyophilized from 30% acetic acid. The structure of the products was verified by amino acid analysis and by gas-phase microsequencing. The products were pure as ascertained by HPLC under two different column conditions.

TABLE 1

Schedule for solid-phase peptide synthesis

| Operation No. | Step No. | Operation | No. Times | Mix Time (Min) |
|---|---|---|---|---|
| I | | Deprotection | | |
| | 1 | $CH_2Cl_2$ | 3 | 1 |
| | 2 | Prewash 50% $TFA/CH_2Cl_2$* | 1 | 1 |
| | 3 | Deprotection 50% $TFA/CH_2Cl_2$* | 1 | 30 |
| | 4 | $CH_2Cl_2$ | 5 | 1 |
| | 5 | EtOH | 2 | 1 |
| | 6 | $CH_2Cl_2$ | 5 | 1 |
| II | | Neutralization | | |
| | 1 | 10% Diisopropylethyl-amine/$CH_2Cl_2$ | 3 | 2 |
| | 2 | $CH_2Cl_2$ | 5 | 1 |
| III | | Coupling | | |
| | 1 | Boc-amino acid (3 eq.)/$CH_2Cl_2$** | 1 | 0.5 |
| | 2 | $DCC/CH_2CL_2$ coupling** | 1 | 120 |
| | 3 | $CH_2Cl_2$ | 5 | 1 |
| | 4 | EtOH | 2 | 1 |
| | 5 | $CH_2Cl_2$ | 5 | 1 |
| IV | | Monitoring*** | | |

*50% $TFA/CH_2Cl_2$ was substituted with 50% $TFA/CH_2Cl_2$ containing 0.05% ethanedithiol after the methionine residue had been coupled to the resin.
**Boc—Asn was coupled by the the HOBt/DCC Method as described by Mojsov et al., J. Org. Chem. 45, 555 (1980). Briefly, Boc—Asn or Boc—Gln (4 eq.) and HOBt (4 eq.) were dissolved in a minimum amount of DMF and cooled in an ice water bath for 10 minutes. DCC (4 eq., 200 mg/ml in $CH_2Cl_2$) was precooled to 0° C. for 10 minutes and mixed with the Boc-aa/HOBt DMF solution. The mixture was kept in ice water for 10 minutes and then transferred to the reaction vessel.
***The efficiency of coupling was monitored by the ninhydrin color reaction test. If the coupling was incomplete, coupling operations III-1 to III-5 were repeated.
TFA = trifluoracetic acid
DMF = N,N—dimethylformamide
aa = amino acid
HOBt = 1-hydroxybenzotriazole monohydrate The N-protected amino acids used in the above solid phase peptide synthesis are defined as follows:
Boc - Ser (Bzl)=t-Boc-O-benzyl-L-serine
Boc - Cys (4-MeBzl)=t-Boc-S-4-methylbenzyl-L-cysteine
Boc - Phe=t-Boc-L-phenylalanine
Boc - Gly=t-Boc-glycine
Boc - Arg(Tos)=t-Boc-$N^g$-tosyl-L-arginine
Boc - D-Arg (Tos)=t-Boc-$N^g$-tosyl-D-arginine
Boc - Ile=t-Boc-L-isoleucine
Boc - Met=t-Boc-L-methionine
Boc - Asp(OBzl)=t-Boc-L-aspartic acid-$\beta$-benzyl ester
Boc - Ala=t-Boc-L-alanine
Boc - Gln=t-Boc-L-glutamine
Boc - Gln-ONP=t-Boc-L-glutamine-p-nitrophenyl ester
Boc - Leu=t-Boc-L-leucine
Boc - Asn=t-Boc-L-asparagine
Boc-Tyr(2,6-diClBzl)=t-Boc-O-2,6-dichloro-benzyl-L-tyrosine

EXAMPLE 1

[$Arg^1$, $arg^2$]-AP-II-$NH_2$ was synthesized and biologically tested as follows:
A. Synthesis The peptide was assembled on a p-Methylbenzhydrylamine Resin with a substitution of 0.35 mmol $NH_2$/g resin using the standard solid phase peptide synthesis method as described above. The couplings of the Boc-amino acid (3 equiv.) were carried out in dichloromethane/DMF with dicyclohexylcarbodiimide (3 equiv.), except for Gln, where Boc-Gln-ONp (2.5 equiv.) was used. The coupling reaction was monitored for completion by the ninhydrin test. Trifluoracetic acid/dichloromethane (1:1, v/v) was used to remove the Boc-group, followed by neutralization with 10% diisopropylethylamine/dichloro-methane (v/v). Following is the sequence of [$Arg^1,arg^2$]-AP-II-$NH_2$ showing the side chain protecting groups (in parentheses) used:

-Arg(Tos)-Arg(Tos)-Cys(4-MeBzl)-Phe-Gly-Gly-Arg(Tos)-Ile-Asp(OBzl)-Arg(Tos)-Ile-Gly-Ala-Gln-Ser(Bzl)-Gly-Leu-Gly-Cys(4MeBzl)-Asn-Ser(Bzl)-Phe-Arg(Tos)-

The peptide was removed from the resin using HF/anisole (9:1, v/v) and 2-mercaptopyridine (150 mg/g of peptide-resin) at 0 degrees for 1 hour. The crude free peptide was extracted with 30% acetic acid/water and lyophilized.

B. Purification and Cyclization

The crude material was purified by HPLC on a Waters RP μ-Bondapak C-18 column (19 mm×150 mm). A linear gradient of 15–35% acetonitrile (0.05% TFA) in water (0.05% TFA) over 30 minutes was used. The flow rate was 9 ml/min. and the eluent was monitored at a wavelength of 225 nm. Desired fractions were collected, analyzed and lyophilized. The cyclization of the peptide was done by stirring the peptide in a 0.1M ammonium bicarbonate buffer (pH 7.8) at a concentration of 0.1 mg/ml for 20 hours. The solution was then acidified to pH 2 with acetic acid and lyophilized. The cyclized peptide was purified using the conditions described above and its purity was analyzed by HPLC on a Vydac C-18 reversed phase column (4.6 mm×250 mm) using a gradient of 15–35% acetonitrile (0.05% TFA) in water (0.05% TFA). The flow rate was 1 ml/min. Amino acid analysis and peptide sequencing were performed to verify the integrity of the purified peptide.

C. Bioassay

C.1. Rabbit aorta relaxation assay.

Spiral strips of rabbit thoracic aorta under 1 g tension were continuously perfused at 10 μg/min. with oxygenated Krebs-Henseleit solution (37° C.) Resting tone was induced by $4.5 \times 10^{-8}$M norepinephrine. The effects of test peptides were determined by application with micropipets to the stream of medium flowing over the tissues, using atriopeptin III as standard.

C.2. Receptor binding assay.

The relative binding affinities for an atrial peptide receptor on rabbit lung membranes were determined for the atrial peptide analogs. Various concentrations of the test peptide were incubated with $^{125}$I-labeled AP-III and a rabbit lung membrane preparation. The concentration of peptide which displaced 50% membrane-bound radiolabeled AP-III was the $IC_{50}$ value (50% inhibitory concentration) for that peptide. The $IC_{50}$ value was compared to that of unlabeled AP-III as standard to determine the relative binding affinity for the peptide of interest, i.e. relative binding affinity for the peptide is $IC_{50}$ for AP-III/$IC_{50}$ for the peptide.

C.3. Natriuresis.

The natriuretic activity and the change in renal blood flow were determined in male pure-bred beagles (12–16 kg) approximately 12–18 months of age under sodium pentobarbital anesthesia. A cuffed endo-tracheal tube was inserted and inflated with air. The femoral artery is catheterized and the blood pressure and heart rate are monitored through pressure transducer. The right kidney, ureter and renal artery are exposed through a retroperitoneal incision. The ureter is catheterized and urine is then collected at 5 minute intervals. An electromagnetic flow probe is placed around the renal artery. Proximal to the kidney and distal to the aorta, and L-shaped 22-gauge needle with attached tubing is inserted into the renal artery in a direction opposite to blood flow. The test peptide was injected in buffered saline solution (pH ca. 7.4) and flushed with 1 ml of heparin (10 units per ml). The test peptide was injected at four different concentration levels, namely one μg, 3 μg, 10 μg and 30 μg, in order to obtain a dose response curve. The injections were done in a periodicity of 15–30 minutes depending on the clearance time of the previously injected test sample. The dog is sacrificed upon conclusion of the test. The infused kidney was then removed and weighed. Urine samples were measured for volume, and sodium concentration was measured by flame photometry.

In a similar manner, substitutions of [$arg^1$], [$arg^1,arg^2$], [$D-arg^1$], [$D-arg^1,D-arg^2$], leu-[$arg^1,arg^2$] and ser-leu-[$arg^1,arg^2$] were made for N-terminal $ser^1$-$ser^2$ in several of the atriopeptins I, II and III in the free acid and amide forms and biologically tested as above. For comparison, [$arg^4$], [$lys^1,lys^2$] and [$his^1, his^2$] analogs of AP-II-$NH_2$ also were prepared and biologically tested. The following Table 2 sets forth the results of these tests.

TABLE 2

| Relative Biological Activity of Atrial Peptides | | | | |
|---|---|---|---|---|
| Peptide | RA | RRA | ΔRBF | $\Delta U_{Na}V$ | (N) |
| AP-III | 1.0 | 1.0 | 1 | 1 | |
| [$R^1,R^2$]-AP-III | | 1.6 | 2 | | 2 |
| [—,$R^2$]-AP-III | 3.0 | 1.8 | 1–2 | 1–2 | 5 |
| AP-II-$NH_2$ | 2.4 | 3.2 | 2 | 2 | 5 |
| [$R^1,R^2$]-AP-II-$NH_2$ | 4.5 | 4.4 | 1.5–3 | 10 | 4 |
| [—,$R^2$]-AP-II-$NH_2$ | 3.7 | 4.0 | 1–4 | 1–4 | 2 |
| [$D-R^1,D-R^2$]-AP-II-$NH_2$ | 2.3 | 4.6 | 13 | 20 | 4 |
| [—,$D-R^2$]-AP-II-$NH_2$ | 2.9 | 5.5 | 1–3 | 1–2 | 2 |
| [$R^1,R^2$]-AP-II-NHEt | 3.1 | 2.3 | 40 | 10 | |
| AP-I-$NH_2$ | 0.14 | 0.4 | | | |
| [$R^1,R^2$]-AP-I-$NH_2$ | 0.031 | 1.4 | 0.2–0.5 | 0.1 | |
| [—,$R^2$]-AP-I-$NH_2$ | 0.023 | 0.6 | 0.2–0.4 | 0.3 | |
| AP-I | 0.012 | 0.2 | | | |
| S-L-[$R^1,R^2$]-AP-II-$NH_2$ | 1.4 | 4.7 | 2 | 20 | 4 |
| L-[$R^1,R^2$]-AP-II-$NH_2$ | 2.4 | 4.8 | | | |
| [$H^1,H^2$]-AP-II-$NH_2$ | .05 | .17 | | | |
| [$K^1,K^2$]-AP-II-$NH_2$ | .07 | 2.2 | 0.25–0.5 | 0.5–1.0 | 2 |
| [$R^4$]-AP-II-$NH_2$ | .016 | 3.1 | | | |

RA = Rabbit aorta relaxation assay
RRA = Rabbit lung receptor assay
ΔRBF = Change in renal blood flow
$\Delta U_{Na}V$ = Change in urinary sodium excretion
(N) = Number of animals
R = Arginine
S = Serine
L = Leucine
H = Histidine
K = Lysine
Et = Ethyl It will be seen from the above results that substitution of the N-terminal $Ser^1$-$ser^2$ in AP-I, II and III with one or two arginine residues results in a general enhancement in biological activity. Only in the two isolated cases of the aorta relaxation assay for the N-terminal arginine substituted AP-I-amide was a significant decrease in activity observed. However, even in the latter instances the N-terminal arginine substituted AP-I-amide had greater aorta relaxation activity than the corresponding free acid form of AP-I (AP-I-OH). By way of comparison, analogous substitutions with N-terminal lysine or histidine, or substitution with arginine in the position immediately following rather than preceding the first cysteine residue, resulted in significant loss of the biological activity. The latter peptide was relatively inactive in the rabbit aorta relaxation assay even though it binds the receptor on rabbit lung membrane.

The novel synthetic peptides of this invention can be administered as diuretics, natriuretics, vasodilators, smooth muscle relaxants, and hypotensive agents to patients in need of such treatments. The amount of peptide which would normally be administered is primarily dependent upon the physical characteristics of the recipient and the severity of the pathological condition to be treated. The amount to be administered must be an effective amount, that is, an amount which is medically beneficial but does not present toxic effects which overweigh the advantages which accompany its use. The preferable route is parenteral, especially intravenous. Intravenous administration of the peptide in solution with normal physiologic saline is illustrative. Other suitable formulations of the active peptide in pharmaceutically acceptable diluents or carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa. Intranasal administration such as described in copending application Ser. No. 732,781, filed May 10, 1985, and assigned to a common assignee, also is suitable. The disclosure of said application is incorporated herein by reference.

Various other examples will be apparent to the person skilled in the art after reading the present disclosure without departing from the spirit and scope of the invention, and it is intended that all such other examples be included within the scope of the appended claims.

What is claimed is:

1. A synthetic peptide having potent natriuretic activity comprising the following amino acid sequence:

$R_1$-cys-phe-gly-gly-arg-X-asp-arg-ile-gly-ala-gln-ser-gly-leu-gly-cys-asn-$R_2$ wherein
$R_1$ = arg, arg-arg, leu-arg-arg, ser-leu-arg-arg, D-arg, D-arg-D-arg,
$R_2$ = ser-phe, ser-phe-arg, ser-phe-arg-tyr,
X = met, ile,
or the physiologically acceptable salts, esters or amides thereof.

2. A peptide of claim 1 in the oxidized form having a disulfide bond between the two cysteine residues.

3. A peptide of claim 1 in which the amide is a mono- or di-lower alkyl substituted amide.

4. A peptide of claim 1 in which X is ile.

5. A peptide of claim 2 in which X is ile.

6. A peptide of claim 5 in which $R_2$ is ser-phe-arg-tyr.

7. A peptide of claim 5 in which $R_2$ is ser-phe-arg in the amide form.

8. A peptide of claim 3 in which the amide is ethylamide.

9. A peptide of claim 7 in which the amide is ethylamide.

10. A peptide of claim 1 in which $R_1$ is arg.

11. A peptide of claim 1 in which $R_1$ is arg-arg.

12. A peptide of claim 2 in which $R_1$ is arg.

13. A peptide of claim 2 in which $R_1$ is arg-arg.

14. A peptide of claim 11 in which $R_2$ is ser-phe-arg in the amide form.

15. A peptide of claim 14 in which the amide is ethylamide.

16. A method for producing natriuresis, diuresis, vasodilation or change in renal blood flow in a mammal comprising administering to said mammal a therapeutically effective amount of a peptide as defined in claim 1.

* * * * *

UNITED STATES PATENT AND TRADEMARK OFFICE
CERTIFICATE OF CORRECTION

PATENT NO. : 4,716,147
DATED : Dec. 29, 1987
INVENTOR(S) : Foe S. Tjoeng, Kam F. Fok and Steven P. Adams It is certified that error appears in the above—identified patent and that said Letters Patent is hereby corrected as shown below:

In the title on the title page, "AIRIAL" should read --ATRIAL--.

In the title in col. 1, "AIRIAL" should read --ATRIAL--.

Signed and Sealed this

Second Day of August, 1988

Attest:

DONALD J. QUIGG

*Attesting Officer*　　　　*Commissioner of Patents and Trademarks*